United States Patent
Burnes et al.

(10) Patent No.: US 7,248,918 B2
(45) Date of Patent: Jul. 24, 2007

(54) SYSTEM AND METHOD FOR SUPPLYING A PATIENT REMINDER ALERT FROM AN IMPLANTABLE MEDICAL DEVICE

(75) Inventors: John E. Burnes, Andover, MN (US); Luc R. Mongeon, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 647 days.

(21) Appl. No.: 10/423,202

(22) Filed: Apr. 25, 2003

(65) Prior Publication Data

US 2004/0215269 A1    Oct. 28, 2004

(51) Int. Cl.
*A61N 1/00* (2006.01)
(52) U.S. Cl. ......................................................... 607/2
(58) Field of Classification Search .................... 607/2, 607/3, 5, 6, 18–20, 27, 32, 59, 60, 62, 63; 600/300, 508, 509, 515, 518, 522, 523; 340/539.12, 340/573.1, 573.3
See application file for complete search history.

(56) References Cited

U.S. PATENT DOCUMENTS

| 4,625,730 | A | * | 12/1986 | Fountain et al. ................ 607/4 |
| 4,871,351 | A | * | 10/1989 | Feingold ....................... 604/66 |
| 5,113,869 | A | * | 5/1992 | Nappholz et al. ........... 600/508 |
| 5,607,459 | A | | 3/1997 | Paul et al. |
| 5,609,615 | A | | 3/1997 | Sanders et al. |
| 5,709,712 | A | | 1/1998 | Paul et al. |
| 5,987,356 | A | | 11/1999 | DeGroot |
| 6,067,473 | A | | 5/2000 | Greeninger et al. |
| 6,082,367 | A | | 7/2000 | Greeninger et al. |
| 6,128,528 | A | | 10/2000 | Ericksen et al. |
| 6,273,856 | B1 | * | 8/2001 | Sun et al. .................... 600/300 |
| 6,354,299 | B1 | * | 3/2002 | Fischell et al. ............. 128/899 |
| 6,370,433 | B1 | * | 4/2002 | Hartlaub et al. .............. 607/32 |
| 6,497,655 | B1 | | 12/2002 | Linberg et al. |
| 2002/0123673 | A1 | | 9/2002 | Webb et al. |
| 2003/0041866 | A1 | | 3/2003 | Linberg et al. |

FOREIGN PATENT DOCUMENTS

WO     WO 01/43823 A2    6/2001

\* cited by examiner

*Primary Examiner*—Robert Pezzuto
*Assistant Examiner*—Yun Haeng Lee
(74) *Attorney, Agent, or Firm*—Michael C. Soldner; Girma Wolde-Michael (57) ABSTRACT

An implantable medical device (IMD) provides an alert to a patient that has the IMD implanted in their body. The alert is used to remind the patient to schedule and/or proceed to a follow-up physician visit. The reminder is also used to remind the patient to initiate a remote communication so that stored data or other information may be transmitted to a remote computer network or other communication node.

40 Claims, 4 Drawing Sheets

SYSTEM AND METHOD FOR SUPPLYING A PATIENT REMINDER ALERT FROM AN IMPLANTABLE MEDICAL DEVICE

FIELD OF THE INVENTION

The present invention relates to implantable medical devices (IMDs) and, more particularly, to an IMD that includes an alert function that reminds the patient into which the IMD is implanted to check in with a doctor or follow-up clinic and/or initiate a remote communication session.

BACKGROUND OF THE INVENTION

Various types of devices have been developed for implantation into the human body to provide various types of health-related therapies and/or monitoring. Examples of such devices, generally known as implantable medical devices (IMDs), include cardiac pacemakers, cardioverter/defibrillators, cardiomyostimulators, various physiological stimulators including nerve, muscle, and deep brain stimulators, various types of physiological monitors, and drug delivery systems, just to name a few. Some IMDs include varying amounts of electronic memory that may be used to store not only device operating and control software, but to store various types of patient- and device-related data. In addition, some of these same IMDs may include signal processing and telemetry circuitry, which allows some or all of the data stored in the memory to be transmitted to a remote computer network or other communication node, and/or the device to receive and store data transmitted to it remotely from a computer network or other communication node.

In many cases, after an IMD has been implanted in a patient, the patient may need to have periodic follow-up visits with a doctor or other type of practitioner. Alternatively, or in addition to periodic follow-up visits, patients with IMDs may need to periodically initiate a communication with a doctor or other type of practitioner at a medical facility or clinic, or periodically initiate a remote communication, such as described above, between the IMD and a remote network or other communications node. These periodic visits and/or communications, allow doctors or other practitioners to check the IMD and patient to determine, for example, whether or not the IMD is operating as programmed or perhaps should be programmed differently. These periodic visits and/or communications also allow, among other things, doctors or other practitioners to analyze some or all of the data stored in and/or transmitted from the IMD. These data can provide the doctor or other practitioner with various types of physiological data about the patient, and may also be used to determine whether or not the IMD is functioning properly.

Unfortunately, in some instances patients do not schedule a follow-up visit or do not call in or otherwise initiate a remote communication. In such instances, extra time and effort may be expended by medical or other personnel in contacting those patients that failed show up for, or call in to schedule, a follow-up visit, and/or otherwise failed to initiate a remote communication. This can result in increased medical-related and administrative costs, and a reduced level of medical care. Moreover, if the patient's IMD is configured to store various types of data related to certain physiological events, and the patient experiences a relatively high number of these events, the possibility exists that the IMD memory may become full and the IMD may overwrite some previously stored data before it has been transmitted to the computer network or other communication node. This can result in the loss of important physiologic data that may be helpful in the long term care, therapy, and/or treatment of the patient. This can also result in increased time, effort, and cost in requesting additional information from the patient regarding potential physiological events, should some data be overwritten. There is also a possibility of a loss of data accuracy if the patient is the only source of those data.

Hence, there is a need for a system and method that provides an alert to a patient having an IMD that reminds the patient to schedule and/or proceed to a follow-up physician visit, and/or to initiate a remote communication to transmit stored data or other information to a remote computer network or other communication node. The present invention addresses one or more of these needs. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

In one exemplary embodiment, an implantable medical device (IMD) includes a timer circuit, a memory circuit, and a controller circuit. The timer circuit is operable to supply a time signal, and the memory circuit is operable to store data representative of a check time. The controller circuit is in operable communication with the timer circuit and the memory circuit and is operable to supply an alert signal at a time relative to the check time stored in the memory circuit.

In another exemplary embodiment, a system for supplying a reminder to a patient having an implantable medical device (IMD) includes an IMD and a radio frequency (RF) receiver. The IMD includes a timer circuit, a memory circuit, a controller circuit, an RF signal source, and an RF emitter. The timer circuit is operable to supply a time signal. The memory circuit is operable to store data representative of a check time. The controller circuit is in operable communication with the timer circuit and the memory circuit and is operable to issue an alert signal at a time relative to the IMD check time stored in the memory circuit. The RF signal source is coupled to receive the alert signal and is operable, in response thereto, to supply an RF signal, and the RF emitter is coupled to receive the RF signal and is operable, in response thereto, to emit the RF signal. The RF receiver is configured to receive the emitted RF signal and is operable, in response thereto, to issue a patient reminder signal.

In yet another exemplary embodiment, an implantable medical device (IMD) includes a memory circuit and a controller circuit. The memory circuit has a plurality of memory registers adapted to receive and store data therein. The controller circuit is in operable communication with the memory circuit and is operable to (i) determine content of one or more of the memory registers and (ii) supply one or more alert signals based at least in part on the determined content of one or more of the memory registers.

In still another exemplary embodiment a method of reminding a patient having an implantable medical device implanted in their body to take an action includes determining content of one or more memory registers, and supplying one or more alert signals to the patient based at least in part on the determined content of one or more of the memory registers.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the drawings. In this regard, before proceeding with the detailed description, it is to be appreciated that the described embodiment is not limited to use in conjunction with a specific type of implantable medical device (IMD). Thus, although the present embodiment is, for convenience of explanation, depicted and described as being implemented in an implantable cardioverter-defibrillator (ICD), it will be appreciated that it can be implemented in various other IMDs.

Figure 1:
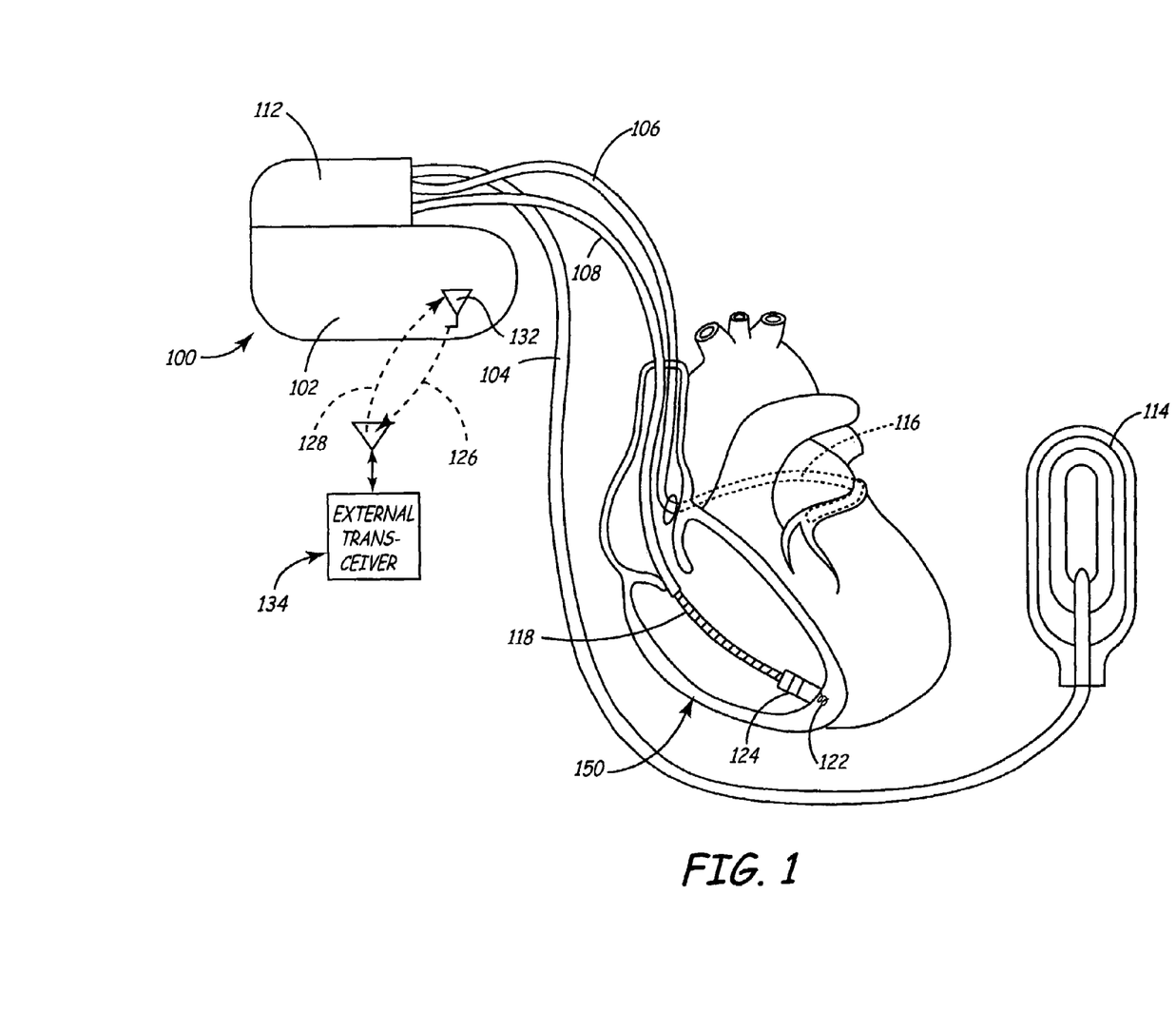
FIG. 1 is a perspective view of an implantable cardio-defibrillator coupled to a heart and which is exemplary of one type of implantable medical device (IMD) that may incorporate an embodiment of the present invention.

Turning now to the description and with reference first to FIG. 1, a simplified representation of an ICD 100 and its connection to a patient heart 150 is shown. The ICD 100 includes a housing 102 and a plurality of leads, including a first lead 104, a second lead 106, and a third lead 108. The housing 102 is preferably formed of a suitable, internal body compatible material that has been approved for medical use, such as, for example, titanium. The housing is preferably hermetically sealed, so that it is substantially impervious to body fluids, and is suitably physiologically shaped to substantially avoid any sharp edges, so that tissue damage during and after implantation can be substantially avoided. The housing 102 includes a connector header 112, which includes separate connector ports and feedthroughs (neither are shown), at least one for each lead 104–108. The connector ports each electrically couple one of the leads 104–108 to one of the feedthroughs, which in turn electrically couples the connector port to the associated circuitry housed within the housing 102. A detailed description of at least a portion of this circuitry is provided further below.

The first, second, and third leads 104–108, each of which include a plurality of conductors, extend from the housing 102 and include first, second, and third electrodes, 114, 116, and 118, respectively, that can be used for pacing, sensing, and/or cardioversion/defibrillation. When implanted in a patient, the first lead 104 extends subcutaneously from the housing 102, and the first electrode 114 is mounted in the patient's chest cavity proximate the heart 150. The second lead 106 extends subcutaneously from the housing 102 and into the patient heart 150. Specifically, the second lead 106 extends transvenously into the heart 150 and, more particularly, into the coronary sinus and down any cardiac vein accessible from the coronary sinus. The second electrode 116 is disposed in the heart 150 such that it extends from a point within the opening of the coronary sinus to the vicinity of the left ventricle. Similarly, the third lead 108 extends transvenously into the heart 150 and, more particularly, into the right ventricular chamber, in which the third electrode 118 is disposed. As is generally known, cardioversion-defibrillation shocks may be applied, when needed, between selected pairs of the first 114, second 116, and third 118 electrodes, according to any one of various defibrillation regimens. It is additionally noted that, in the depicted embodiment, the third lead 108 is also terminated with a pair of ventricular pace/sense electrode 122 and 124. These ventricular pace/sense electrodes are used to provide cardiac pacing pulses, and may be additionally employed to provide near field and/or far field EGM ventricular sensing capabilities.

Figure 2:
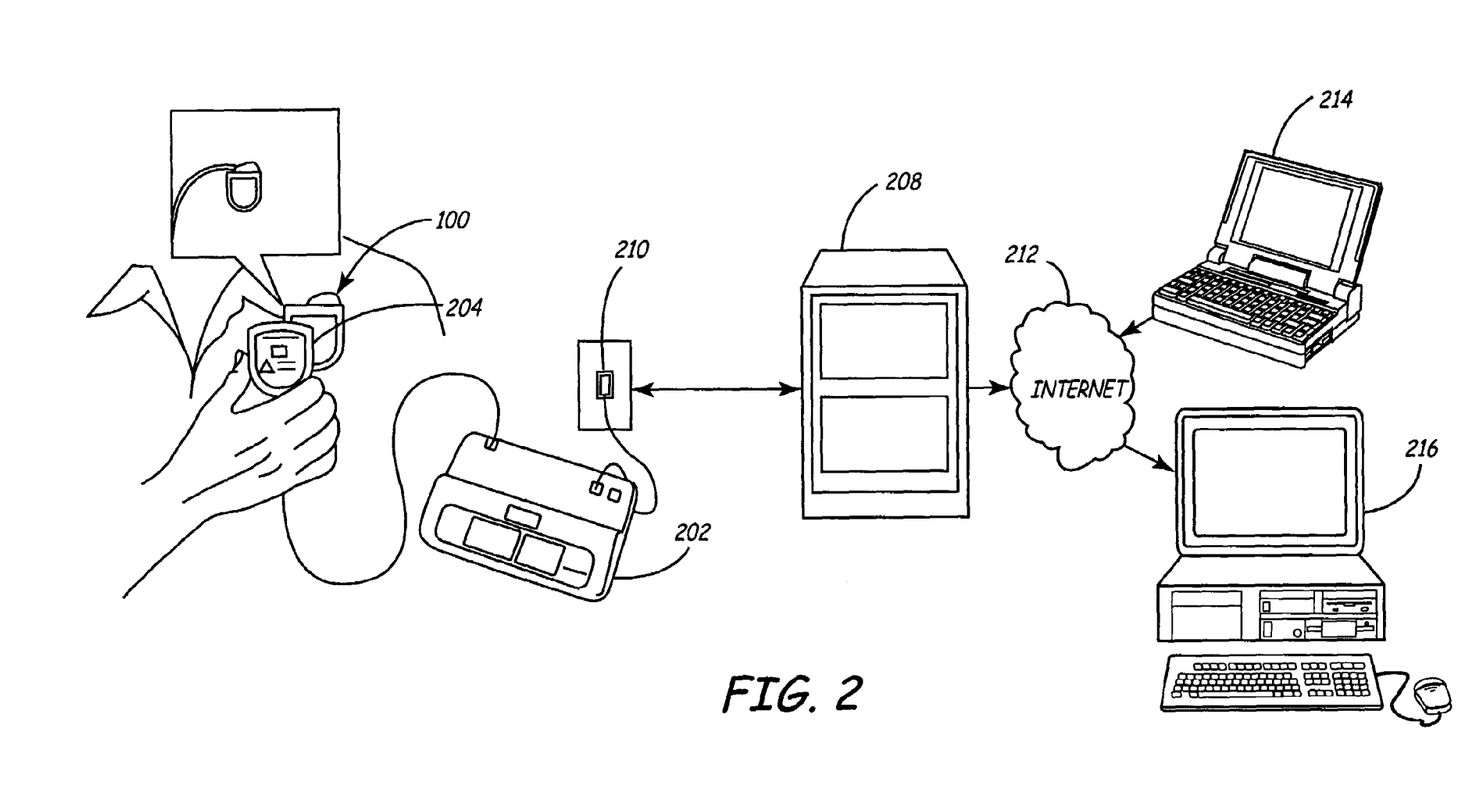
FIG. 2 depicts the IMD of FIG. 1 in communication with a secure server computer via a transceiver device.

As FIG. 1 additionally shows, the ICD 100 is capable of both transmitting 126 and receiving 128 data. This may be accomplished in any one of numerous ways, but in the depicted embodiment this is accomplished via telemetry transmission using any one of numerous known telemetry protocols. Thus, the ICD 100 includes a small antenna 132 that is used, in conjunction with other circuitry within the ICD housing 102 that is described in more detail below, to transmit 126 data to, and to receive 128 data from, one or more external transceivers 134. The data that the ICD 100 transmits to, and receives from, the external transceiver 134, will depend, at least in part, on the type and purpose of the transceiver 134. For example, the transceiver 134 may be a programming device that a physician or other practitioner uses to program or reprogram the overall operation, or portions thereof, of the ICD 100. Alternatively, the transceiver 134 may be a monitoring device that is used to interrogate the ICD 100 and, in response to the interrogation, receive various data from the ICD 100 for subsequent transmission. Moreover, as will be described in more detail further below, the transceiver 134 could be a device that supplies various types of patient reminder alerts. An exemplary embodiment of the second type of transceiver 134 and its interconnection to external devices is shown in FIG. 2 and will now be described in more detail.

The transceiver 134 includes a main monitor controller 202 and a monitor antenna 204. In response to an input from a user such as, for example, pressing a button or other input device (not shown) on the monitor controller 202, the monitor controller 202 begins transmitting interrogation signals to the monitor antenna 204. The monitor antenna 204 emits these interrogation signals, which are in turn received by the ICD antenna 132. Again, as will be described in more detail below, in response to the interrogation signals received by the ICD antenna 132, the ICD 100 transmits various types of device-related data and physiologic-related data stored in the ICD 100, via the antenna 132. The data transmitted from the ICD 100 is received by the monitor antenna 204 and is transferred to the monitor controller 202.

Once the data transmission from the ICD 100 to the transceiver 134 is complete, or in conjunction with the data transmission, the monitor controller 202 establishes communication with a secure computer network 208. This communication may be established in any one of numerous ways. For example, in the depicted embodiment the monitor controller 202 is coupled to a telephone jack 210 and is programmed to dial a specified telephone number that establishes communication with the secure network 208.

Alternatively, it will be appreciated that the communication could also be established via an interconnected computer network such as the Internet 212. No matter how the data is transferred to the secure network 208, once it is there, the data is available for use by physicians and other practitioners, and may additionally be available to other persons.

In particular, as FIG. 2 additionally illustrates, physicians and other practitioners may each use a computer 214 to log into the secure network 208 via, for example, the Internet 210, and obtain the data transmitted from the ICD 100 to the secure network 208. In addition, the patient into which the ICD 100 is implanted, as well as other persons the patient so designates, can access some or all of the data transmitted from the patient's ICD to the secure network 208. To do so, the patient or other designated persons may each use a computer 216 to log into the secure network 208 via, for example, the Internet 212, and access a personal website. The data, or portions thereof, may then be accessed via this personal website.

Figure 3:
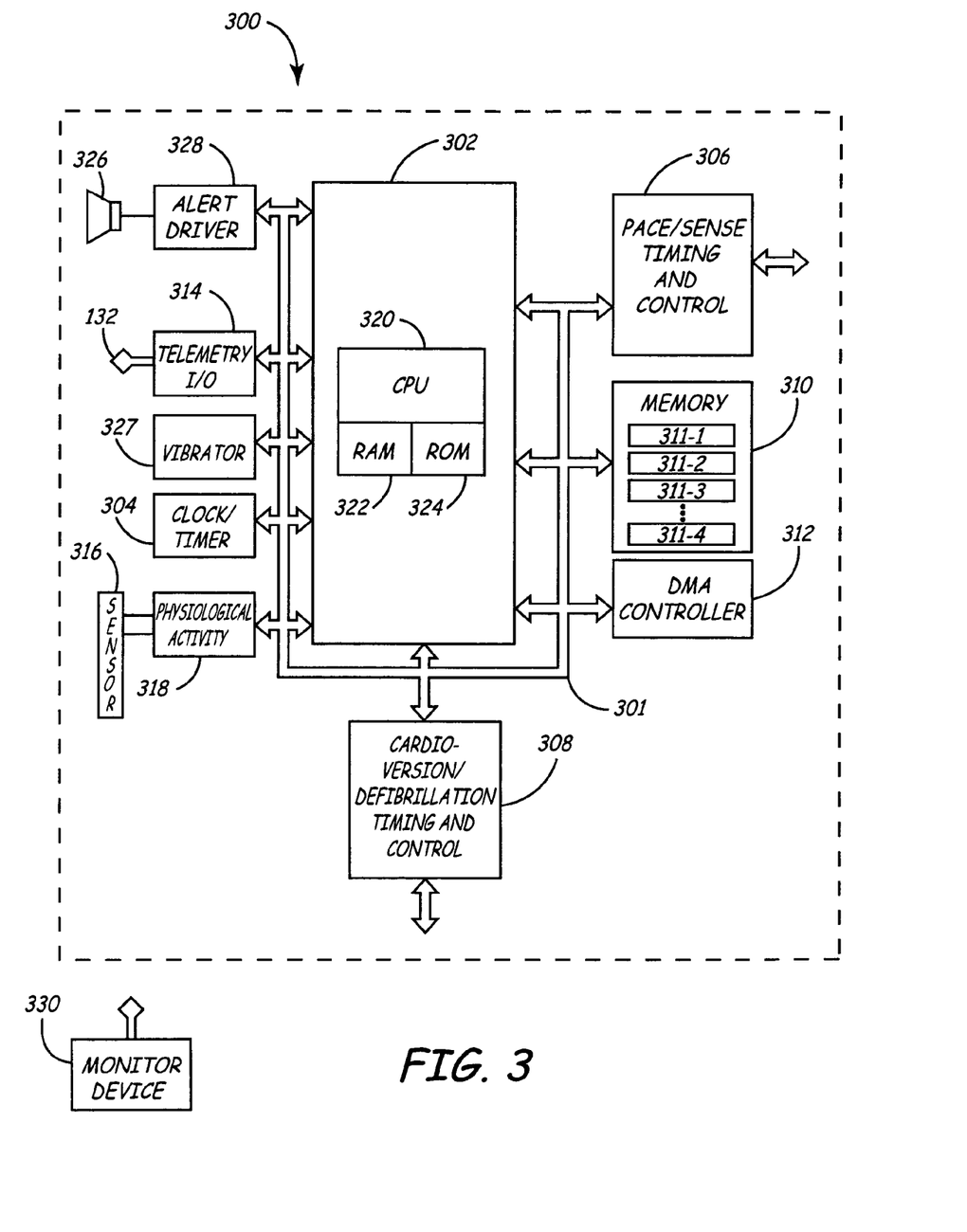
FIG. 3 is a functional block diagram of an exemplary circuit architecture that may be included in the IMD of FIG. 1.

As was noted above, the ICD 100 includes circuitry within the housing 102 that is used to control the overall operation of the ICD 100. At least a portion of this circuitry is illustrated in FIG. 3, and will now be described in detail. The circuitry 300 illustrated in FIG. 3 includes a controller circuit 302 and various other functional circuit blocks 304–318 that are in operable communication with, and which may be operated under control of, the controller circuit 302 via, for example, a common communications data bus 301. It will be appreciated that the circuitry depicted in FIG. 3 is merely exemplary of a particular architecture, and that numerous other circuit architectures may be used to implement the operation of the ICD 100. The controller circuit 302 includes, among other things, a CPU (central processing unit) 320, which may include on-board RAM (random access memory) 322, and on-board ROM (read only memory) 324. The CPU 320 may be any one of numerous known general purpose processors or an application specific processor that operates in response to program instructions. Such program instructions may be stored in either or both the RAM 322 and the ROM 324. For example, the operating system software may be stored in the ROM 324, whereas various operating mode software routines and various operational parameters may be store in the RAM 322. It will be appreciated that this is merely exemplary of one scheme for storing operating software and software routines, and that various other storage schemes may be implemented. It will also be appreciated that the controller circuit 302 may be implemented using various other circuits, not just a programmable processor. For example, digital logic circuits and analog signal processing circuits could also be used.

A clock/timer circuit 304 provides one or more clock and timing signals to the controller circuit 302 and, if needed, to various ones of the other functional blocks 306–318. The clock and timing signals provide for the proper synchronous operation of the various functional circuits that make up the circuitry 300. In addition, one or more of the signals supplied by the clock/timer circuit 304 is used by the controller circuit 302 to determine when one or more patient alert signals should be supplied. This particular functionality of the controller circuit 302 is described in more detail further below. The clock/timer circuit 304 may be any one of numerous known circuits for providing clock and/or timing signals. Non-limiting examples include various types of crystal oscillators, such as a temperature compensated crystal oscillator (TXCO), a micro-computer compensated crystal oscillator (MCXO), and an oven controlled crystal oscillator (OCXO).

A pace/sense timing and control functional circuit 306 and a cardioversion/defibrillation timing and control functional circuit 308 are each coupled to the controller circuit 302 via the communications data bus 301. The pace/sense timing and control functional circuit 306 is programmable and, in response to instructions from the controller circuit, implements various atrial and ventricular pacing operational modes. The pace/sense timing and control circuit 306 may also implement various tachyarrhythmia detection and classification operations. The cardioversion/defibrillation timing and control circuit 308, in response to instructions from the controller circuit 302, delivers cardioversion/defibrillation shock therapy or, if appropriate, pacing pulse therapy, to selected pairs of the first 114, second 116, and third 118 electrodes when an atrial or ventricular fibrillation or flutter, or a malignant high rate tachycardia, is detected.

A memory circuit 310 is in operable communication with the controller circuit 302 via the communications data bus 301. The memory circuit 310 includes a plurality of memory registers 311-1, 311-2, 311-3, . . . 311-N, in which various types of data are stored. The data that the memory circuit 310 stores in its memory registers 311 may include both device-related data and physiological-related data. It will be appreciated that one or more memory circuits 310 may be in operable communication with the controller circuit 302 to store such data. It will also be appreciated that the memory circuit 310 could be integrally formed as part of the controller circuit 302 and/or CPU 320, RAM 322, and/or ROM 324, or could be part of a device or system that is physically separate from the ICD 100. The data that may be stored in memory circuit 310 include, but are not limited to, various types of patient-related data, and various types of device-related data.

Some or all of the data stored in the memory circuit 310 may be read and, as was discussed above, transmitted to an external transceiver 134 (see FIG. 1). Moreover, as was also briefly discussed above, data may be received from an external transceiver 134 and written into the memory circuit 310. Included among the data that is received and written into the memory circuit 310 are one or more check times. These check time data may be representative of either, or both, the previous time, or the next time, that stored data was, or should be, read from the memory circuit 310 and transmitted to an external transceiver 134. These check time data may additionally, or alternatively, be representative of either, or both, the previous time, or the next time, that the patient did, or should, visit their physician or other health care practitioner. The memory circuit 310 may also store data that may be used when providing the patient an alert signal. For example, one or more of the memory circuit registers 311 may store audio frequency data that, when properly processed, may be used to supply a signal in the audio frequency spectrum. The stored audio frequency data may be used to supply both speech-related signals (e.g., a voice message) and non-speech-related signals (e.g., a tone or buzzer). The circumstances under which a patient alert signal is provided are discussed in more detail below.

In the depicted embodiment, a DMA (direct memory access) controller 312 is in operable communication with the controller circuit 302. The DMA controller 312, as is generally known, provides direct memory access to memory circuit memory registers 311, or to the RAM 322 or ROM 324, without involving the CPU 320. This can conserve battery power and simplify data read and write operations.

It will be appreciated that the DMA controller 312 could be omitted or could form an integral part of the controller circuit 320.

As was discussed above, the antenna 132 receives the data that is transmitted from, and emits the data that is transmitted to, the transceiver 134. The antenna 132 is coupled to a telemetry input/output (I/O) circuit 314. As its name connotes, the telemetry I/O circuit 314 functions as an input device, or receiver, when the antenna 132 is receiving data transmitted to the ICD 100, and functions as an output device, or transmitter, when data are being transmitted from the ICD 100. The data transmission to and from the ICD 100 is accomplished using radio frequency (RF) waves. Thus, the telemetry I/O circuit 314 includes one or more RF signal sources that may be used to demodulate the data received by the ICD 100, and to modulate the data being transmitted by the ICD 100. The telemetry I/O circuit 314 may also function to decode interrogation signals it receives from an external transceiver 134 and transfer these decoded signals to the controller circuit 302. The controller circuit 302 may then appropriately command the telemetry I/O circuit 314 to be configured to transmit or receive data.

A physiological activity sensor 316 and appropriate circuit 318 are also in operable communication with the controller circuit 302. The physiological activity sensor 316 senses movement or other physiological-related activity of the patient, and supplies signals representative thereof to the physiological activity circuit 318. The sensor 316 may also sense the relative physical position of the patient. For example, the sensor 316 can be configured to supply one or more signals representative of whether the patient is standing, sitting, or lying down. In the depicted embodiment, the sensor 316 is mounted to the ICD housing 102 and may be any one of numerous known sensors useful for providing such signals. In a particular preferred embodiment, the sensor 316 is an accelerometer, which may be a single-axis or multi-axis type accelerometer. In an alternative embodiment, which is depicted in phantom in FIG. 3, the sensor 316 may include, or instead be, external to the housing 102, and sense various other physiologic-related activity. For example, the sensor 316 could include, or instead be, a transthoracic impedance sensor, which detects breathing patterns. In any case, the physiological activity circuit 318 suitably conditions the signals supplied by the sensor 316 and supplies these signals to the controller circuit 302. The controller circuit 302 then uses these signals to determine, among other things, the relative position of the patient and/or whether the patient is in a physiologically active state, such as walking or otherwise moving, and/or in a physiologically quiet state, such as sitting or lying.

A sound emitter, such as a speaker 326, and an appropriate driver circuit 328, are coupled to the controller circuit 302. The driver circuit 328, when supplied with an appropriate alert signal, amplifies the alert signal and supplies it to the speaker 326. In turn, the speaker 326 emits a sound at the frequency of the alert signal supplied to the driver circuit 328. Thus, for example, if the controller circuit 302 supplies a speech-related alert signal to the driver circuit 328, the speaker 326 will emit the speech-related sound. Similarly, if the controller circuit 302 supplies a non-speech-related alert signal to the driver circuit 328, the speaker 326 will emit a non-speech-related sound. As was noted above, the audio frequency signal source from which the controller circuit 302 supplies the alert signal to the driver circuit 328 may be one or more of the memory registers 311. Alternatively, one or more separate, dedicated audio frequency signal sources may be provided.

In addition to, or instead of, emitting a sound, the IMD 300 may also be configured to provide a vibratory stimulus to the patient by causing one or more components within the IMD to vibrate. For example, in the depicted embodiment, the IMD may additionally include a vibrator device 327, which may be coupled to the controller circuit 302 or the driver circuit 328. The vibrator device 327, when supplied with an appropriate alert signal, will physically vibrate, and in turn cause the IMD 300 to vibrate. It will be appreciated that the vibrator device 327 may be any one of numerous known devices for providing this functionality including, but not limited to, an electromechanical resonator.

As was noted above, a patient that has an IMD implanted in them, such as the ICD 100 depicted and described herein, should periodically schedule a visit with their physician or other health care practitioner. Such visits allow the physician to check not only the patient, but to also check the IMD and, if needed or desired, retrieve at least some of the data store in the IMD memory. In addition, patients are also requested to periodically establish a communication with, for example, the secure network 208 so that data stored in the IMD memory can be read from memory and transmitted to the secure network 208. This gives the patient's physician, and other health care practitioners, secure access to the data to track patient and IMD performance, and significantly reduces the likelihood of some of the stored data being overwritten.

To prevent or at least significantly reduce the likelihood that a patient will forget to schedule and/or come in for a visit with their physician or other practitioner, and to additionally prevent or at least significantly reduce the likelihood that stored data are overwritten before being read, the ICD 100 incorporates a patient reminder function. This patient reminder function is illustrated in flowchart form in FIG. 4, and will now be described.

Figure 4:
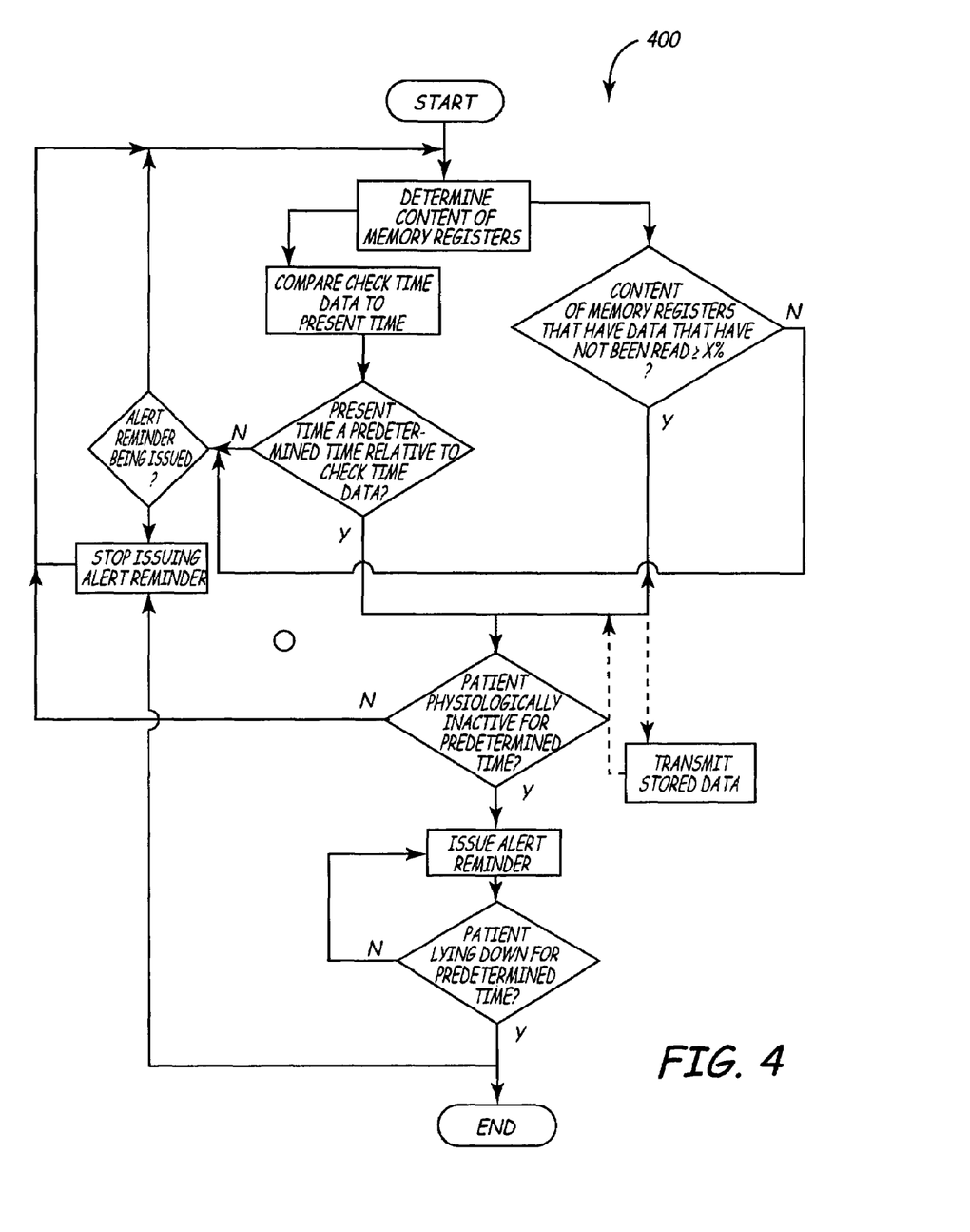
FIG. 4 is a flowchart depicting an exemplary process flow of a patient reminder function implemented by the IMD, communication, and circuit architecture of FIGS. 1, 2, and 3, respectively.

In accordance with the exemplary process 400 shown in FIG. 4, the controller circuit 302 supplies an alert signal to either, or both, the alert driver circuit 324 and the telemetry I/O circuit 314 at certain times and under various circumstances. For example, as was noted above, among the data that the memory circuit 310 stores are one or more check times. These check time data may be representative of either, or both, the previous time, or the next time, that stored data were, or should be, read from the memory circuit 310 and transmitted to an external transceiver 134. These check time data may additionally, or alternatively, be representative of either, or both, the previous time, or the next time, that the patient did, or should, call and/or visit their physician or other health care practitioner. The controller circuit 302 periodically reads this stored check time data and, when needed, will supply an alert signal at a time relative to this stored check time. It will be appreciated that if the check time is representative of the next time an activity should occur this time could be derived using any one of numerous methods. Non-limiting examples include simply using a predetermined amount of time since a previous check time, or using an algorithm or artificial intelligence type methodology that derives the next time from a previous check time and various sensed physiological conditions.

Thus, for example, if the check time stored in the memory circuit 310 is data representative of the previous time that the ICD 100 or patient was checked, or the previous time that an external device read stored data from the ICD 100, the controller circuit 302 will supply an alert signal at a time period after the stored check time. Alternatively, if the check time stored in the memory circuit 310 is representative of the next time the ICD 100 or patient should be checked, or the next time that an external device should read stored data from the ICD 100, the controller will supply an alert signal at a time period relative to the stored check time such as, for example, shortly before the stored check time, at the stored check time, or shortly after the stored check time.

In addition to supplying an alert signal at a time relative to a stored check time, the controller circuit 302 also determines the capacity of the memory circuit 310 and, if necessary, issues an alert signal. In particular, the controller circuit 302 determines whether or not a predetermined percentage of the memory registers 311 have data stored therein that have not been previously read by an external device such as, for example, the transceiver 134. When this predetermined percentage is reached, or at some time period before or after, the controller circuit 302 supplies an alert signal. For example, if the predetermined percentage is 80% of memory circuit capacity, then when 80% of the memory registers 311 are storing data that has not been read by an external device, the controller circuit 302 will supply an appropriate alert signal. Alternatively, as shown in phantom in FIG. 4, rather than supplying an alert signal, the controller circuit 302 can be configured to instead automatically transmit data from the memory circuit 310 to an external device or system. It will be appreciated that the controller circuit 302 can also be configured to both supply an alert signal and automatically transmit the data.

It will be appreciated that the ICD 100 may be configured to supply an alert signal under any one or more of the circumstances described above. It will additionally be appreciated that the alert signal supplied by the controller circuit 302 may vary depending on the particular circumstance for which the alert is being provided. Moreover, it will be appreciated that the frequency, duration, and type of alert signal supplied by the controller 302 for a particular circumstance may vary with time, until the patient takes the action for which the reminder alert is being supplied. For example, the time interval between alert signals may decrease with time until the patient takes the action for which the reminder alert is being supplied. In addition, or alternatively, the type of reminder alert that is supplied may vary. For example, the alert reminder may begin as a non-speech related sound, such as a tone or buzz. At a later time, if the reminder needs to continue being supplied, it may be supplied as a speech-related sound, and later it may be supplied as some type of physically-related perceptible signal or reminder. As a non-limiting example of this latter type of reminder, the ICD 100 may issue some type of low level electrical stimulus to one or more muscles in the patient's body or, as was also discussed above, cause a vibration of one or more components of the ICD 100. It will be appreciated that the order and type of reminders provided may vary and that the order and type just described are merely exemplary various types of reminder alerts, and of any one of numerous combinations of types of reminder alerts that can be supplied.

In addition to the reminder alerts described above, the ICD 100, as was previously mentioned, may also provide a reminder alert via the telemetry I/O circuit 314. For example, as FIG. 3 additionally depicts, an external ICD monitor device 330, which includes an RF antenna 332, may be in operable communication with the telemetry I/O circuit 314. Thus, in addition to, or instead of, the above-described alert reminders, the controller circuit 302 can be configured to supply one or more alert signals to the telemetry I/O circuit 314, which in turn supplies the alert signals, via any one of numerous known appropriate telemetry communication protocols, to the monitor device 330. The monitor device 330, upon receipt of the alert signals will then issue an appropriate reminder alert to the patient. As with the above described reminder alerts, the frequency and type (e.g., audio, visual, vibratory, or combination thereof) of alert signals supplied to the telemetry I/O circuit 314, and thus the reminder alerts issued by the monitor device 330, may vary in frequency, duration, and type. It will be appreciated that the monitor device 330 could be a special purpose monitor, or this functionality could be incorporated into the monitor controller 202 described above and depicted in FIG. 2. For example, the monitor device 330 could be a device carried in, for example, a clothing pocket of the patient.

The ICD 100 may also be configured to supply the reminder alerts when the ICD 100 determines that the patient is in a low physiological activity state. Thus, if the physiologic activity circuit 318 supplies a signal indicating that the patient is in a physiologically active state, the controller circuit 302 will not immediately supply an alert signal, even though it determines that the time or memory capacity criteria are met. Rather, the controller circuit 302 waits until the signal it receives from the physiologic activity circuit 318 indicates that the patient is in a physiologically inactive state such as, for example, standing relatively still, sitting down, or lying down. At that time, or a short time thereafter, the controller circuit 302 will then supply the appropriate alert signal(s). It will also be appreciated that the ICD 100 is preferably configured such that the controller circuit 302 will cease supplying the appropriate alert signal(s) a time period after the patient is in a physiological inactive state if the physiologic sensor 316 senses that the patient is lying down. This latter functionality will ensure that the ICD 100 does not continue supplying reminder alerts when the patient is attempting to sleep.

The controller circuit 302 will continue supplying one or more alert signals until the criterion for which it is supplying the alert signal is no longer valid. For example, if the criterion is one of the above-mentioned patient or device check times, once the patient takes the appropriate action, new check time data will be stored in the memory circuit 310. This new check time data may be transmitted to the ICD 100 from one of the above-described external transceivers 134, and may be done so by the physician or other practitioner at the physician's office, or via remote transmission directly to the ICD 100 or to the ICD 100 via an external transceivers 134.

While an exemplary embodiment(s) has been presented in the foregoing detailed description of the invention, it should be appreciated that a vast number of variations exist. It should also be appreciated that these exemplary embodiments are only examples, and are not intended to limit the scope, applicability, or configuration of the invention in any way. Rather, the foregoing detailed description will provide those skilled in the art with a convenient road map for implementing a preferred embodiment of the invention. It being understood that various changes may be made in the function and arrangement of elements described in an exemplary preferred embodiment without departing from the spirit and scope of the invention as set forth in the appended claims.

What is claimed is:

1. An implantable medical device (IMD), comprising:
   a timer circuit operable to supply a time signal;
   memory circuit operable to store data representative of an IMD check time associated with one of scheduling a physician visit and proceeding to a physician visit; and
   a controller circuit in operable communication with the timer circuit and the memory circuit and for supplying an alert signal at a time relative to the IMD check time stored in the memory circuit.

2. The device of claim 1, further comprising:
an audio frequency signal source coupled to receive the alert signal and operable, in response thereto, to supply an audible frequency signal; and
a sound emitter coupled to receive the audible frequency signal and operable, in response thereto, to emit an audible sound.

3. The device of claim 2 wherein the audio frequency signal source comprises one or more memory registers each having an audio frequency signal stored therein.

4. The device of claim 2, wherein the signal supplied by the audio frequency signal source is a voice message.

5. The device of claim 2, wherein the signal supplied by the audio frequency signal source is a non-speech related sound.

6. The device of claim 1, further comprising:
a radio frequency (RF) signal source coupled to receive the alert signal
and operable, in response thereto, to supply an RF signal; and
an RF emitter coupled to receive the RF signal and operable, in response thereto, to emit the RF signal.

7. The device of claim 6, wherein the RF emitter is an antenna.

8. The device of claim 1, further comprising:
a physiologic activity sensor in operable communication with the controller circuit and operable to supply a signal representative of physiologic activity,
wherein the controller circuit is further operable to supply the alert signal at a time relative to the check time stored in the memory circuit and when the physiologic activity signal indicates physiologic activity is at or below a predetermined threshold.

9. The device of claim 8, wherein the controller circuit is further operable to supply the alert signal at the time relative to the check time and a first time period after the physiologic activity signal indicates physiologic activity is at or below the predetermined threshold.

10. The device of claim 9, wherein the controller circuit is further operable to cease supplying the alert signal a second time period after the first time period.

11. The device of claim 8, wherein the physiologic activity sensor comprises one or more accelerometers that senses physiological activity and relative position.

12. The device of claim 8, wherein the physiologic activity sensor comprises one or more transthoracic impedance sensors.

13. The device of claim 1, wherein the controller circuit is further operable to (i) receive data representative of a new check time and (ii) replace the check time stored in the memory circuit with the new check time.

14. The device of claim 1, wherein the controller is further operable to repeatedly supply the alert signal for a duration time period at a repetition frequency.

15. The device of claim 14, wherein the controller is further operable to vary at least one of the duration time period and the repetition frequency.

16. The device of claim 15, wherein the controller is:
configured to supply one or more of a plurality of types of alert signals; and
further operable to vary the type of alert signal supplied.

17. The device of claim 1, further comprising:
one or more electrodes coupled to the controller circuit and adapted to electrically couple to one or more muscles in a body,
wherein the alert signal is an electrical stimulus deliverable to the one or more muscles via the one or more electrodes.

18. The device of claim 1, further comprising:
a vibrator coupled to receive the alert signal from the controller circuit and operable, in response thereto, to vibrate at least a portion of the IMD.

19. A system for supplying a reminder to a patient having an implantable medical device (IMD), comprising:
an IMD including:
a timer circuit operable to supply a time signal,
a memory circuit operable to store data representative of a check time associated with one of scheduling a physician visit and proceeding to a physician visit,
a controller circuit in operable communication with the timer circuit and the memory circuit and for supplying an alert signal at a time relative to the IMD check time stored in the memory circuit,
a radio frequency (RF) signal source coupled to receive the alert signal and operable, in response thereto, to supply an RF signal, and
an RF emitter coupled to receive the RF signal and operable, in response thereto, to emit the RF signal; and
an RF receiver configured to receive the emitted RF signal and operable, in response thereto, to issue a patient reminder signal.

20. The system of claim 19, wherein the patient reminder signal issued by the RF receiver is an audible sound.

21. The system of claim 20, wherein the audible sound issued by the RF receiver is a voice message.

22. The system of claim 20, wherein the audible sound issued by the RF receiver is a non-speech related sound.

23. The system of claim 22, wherein the IMD further includes:
a radio frequency (RF) signal source coupled to receive the alert signal and operable, in response thereto, to supply an RF signal; and
an RF emitter coupled to receive the RF signal and operable, in response thereto, to emit the RF signal.

24. The system of claim 23, wherein the RF emitter is an antenna.

25. The system of claim 19, further comprising:
a physiologic activity sensor in operable communication with the controller circuit and operable to supply a signal representative of physiologic activity,
wherein the controller circuit is further operable to supply the alert signal at a time relative to the check time stored in the memory circuit and when the physiologic activity signal indicates physiologic activity is at or below a predetermined threshold.

26. The system of claim 25, wherein the controller circuit is further operable to supply the alert signal at the time relative to the check time and a first time period after the physiologic activity signal indicates physiologic activity is at or below the predetermined threshold.

27. The system of claim 26, wherein the controller circuit is further operable to cease supplying the alert signal a second time period after the first time period.

28. The system of claim 25, wherein the physiologic activity sensor comprises one or more accelerometers that senses physiological activity and relative position.

29. The system of claim 25, wherein the physiologic activity sensor comprises one or more transthoracic impedance sensors.

30. The system of claim 19, wherein the controller circuit is further operable to (i) receive data representative of a new check time and (ii) replace the check time stored in the memory circuit with the new check time.

31. The system of claim 19, wherein the controller circuit is further operable to repeatedly supply the alert signal for a duration time period at a repetition frequency.

32. The system of claim 31, wherein the controller circuit is further operable to vary at least one of the duration time period and the repetition frequency.

33. The system of claim 31, wherein the controller circuit is:
configured to supply one or more of a plurality of types of alert signals; and
further operable to vary the type of alert signal supplied.

34. The system of claim 19, wherein the patient reminder signal issued by the RF receiver is a vibration thereof.

35. An implantable medical device (IMD), comprising:
a memory circuit having a plurality of memory registers adapted to receive and store IMD-related data therein; and
a controller circuit in operable communication with the memory circuit and operable to (i) determine content of one or more of the memory registers and (ii) supply one or more alert signals based at least in part on the determined content of one or more of the memory registers, wherein one or more of the memory registers receives and stores data representative of an IMD check time associated with one of scheduling a physician visit and proceeding to a physician visit, and wherein the device further comprises:
a timer circuit in operable communication with the controller circuit and operable to supply a time signal,
wherein the controller circuit supplies the alert signal at a time relative to the IMD check time stored in the memory circuit.

36. The device of claim 35, wherein the controller circuit supplies the alert signal when it determines that the content of a predetermined number of the memory registers is stored data that have not been transmitted to a device external to the IMD.

37. The device of claim 36, wherein the controller circuit is further operable to transmit the contents of one or more of the memory registers.

38. A method of reminding a patient having an implantable medical device (IMD) implanted in their body to take an action, the method comprising:
determining content of one or more memory registers; and
supplying one or more alert signals to the patient from the IMD based at least in part on the determined content of one or more of the memory registers, wherein the content of one or more of the memory registers is a check time associated with one of scheduling a physician visit and proceeding to a physician visit, and the method further comprises:
determining a time relative to the check time; and
supplying the one or more alert signals to the patient from the IMD when the determined time is at least a predetermined time.

39. The method of claim 38, further comprising:
determining whether the content of the memory registers is stored data that have not been read by one or more devices external to the IMD; and
supplying the one or more alert signals to the patient from the IMD when the content of a predetermined number of the memory registers is stored data that have not been transmitted to one or more devices external to the IMD.

40. The method of claim 39, further comprising: automatically transmitting the contents of one or more data registers.

* * * * *